United States Patent [19]

Hoshino et al.

[11] Patent Number: 6,143,510

[45] Date of Patent: *Nov. 7, 2000

[54] MEASURING METHOD USING WHOLE BLOOD SAMPLE

[75] Inventors: Nobuhiro Hoshino; Michiko Kawamoto; Mitoshi Shimamoto, all of Tokyo, Japan

[73] Assignee: Iatron Laboratories Inc., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/624,415

[22] PCT Filed: Jul. 28, 1995

[86] PCT No.: PCT/JP95/01510

§ 371 Date: Mar. 29, 1996

§ 102(e) Date: Mar. 29, 1996

[87] PCT Pub. No.: WO96/04558

PCT Pub. Date: Feb. 15, 1996

[30] Foreign Application Priority Data

Jul. 29, 1994 [JP] Japan .................................. 6-197207

[51] Int. Cl.[7] ..................... G01N 33/543; G01N 33/553; G01N 33/569; G01N 33/576
[52] U.S. Cl. ........................... 435/7.94; 435/2; 435/7.25; 435/7.92; 435/173.9; 435/297.2; 435/339; 436/518; 436/526; 436/172; 436/820
[58] Field of Search .................................. 435/2, 5, 7.25, 435/7.92, 7.94, 287.2, 173.9, 339, 961, 962; 436/503, 518, 520, 526, 534, 172, 811, 820, 824

[56] References Cited

U.S. PATENT DOCUMENTS

| | | |
|---|---|---|
| 4,115,535 | 9/1978 | Giaever . |
| 4,313,734 | 2/1982 | Leuvering . |
| 4,554,088 | 11/1985 | Whitehead et al. ..................... 436/526 |
| 4,851,210 | 7/1989 | Hewett ..................................... 436/548 |
| 4,943,522 | 7/1990 | Eisinger et al. ......................... 436/518 |
| 4,973,669 | 11/1990 | Wands et al. ......................... 435/172.2 |
| 5,200,084 | 4/1993 | Liberti et al. ............................ 436/526 |
| 5,256,532 | 10/1993 | Melnicoff et al. ....................... 436/526 |
| 5,308,775 | 5/1994 | Donovan et al. ........................ 436/518 |

FOREIGN PATENT DOCUMENTS

91/15769  10/1991  WIPO .

OTHER PUBLICATIONS

Tijssen, 1985. *Practice and Theory of Enzyme Immunoassays*, (Burdon et al, eds.), Elsevier, Amsterdam, pp. 329–32, 376.

*Primary Examiner*—Christopher L. Chin
*Assistant Examiner*—James L. Grun
*Attorney, Agent, or Firm*—Sughrue, Mion, Zinn, Macpeak & Seas, PLLC

[57] ABSTRACT

A method for quantitatively measuring analyte in an undiluted whole blood sample is disclosed which involves contacting an undiluted whole blood sample comprising the analyte with magnetically-responsive particles which comprise a first partner which is coated on a magnetically-responsive particulate insoluble carrier, wherein the first partner specifically binds to the analyte to form a first complex of insoluble carrier-first partner-analyte, separating the resulting first complex from the undiluted whole blood sample, thereafter contacting the resulting separated first complex with a second partner which is labelled with a detectable marker and which specifically binds to the analyte to form a second complex of insoluble carrier-first partner-analyte-second partner, and separating the resulting second complex from unbound second partner by washing, and thereafter detecting the marker in the second complex to quantitatively measure the analyte in the undiluted whole blood sample, and wherein the initial contacting occurs for a period of time prior to an end-point of the binding reaction of the first partner and the analyte.

6 Claims, No Drawings

MEASURING METHOD USING WHOLE BLOOD SAMPLE

TECHNICAL FIELD

The present invention relates to a method for measuring a substance to be examined in a whole blood sample using said whole blood sample as it is. More particularly, the present invention relates to a method for measuring a substance to be examined in a whole blood sample using said whole blood sample as it is, without preparing a serum or plasma sample from blood collected from a patient or the like.

BACKGROUND ART

An immunoassay has been widely used when measuring a substance to be examined (analyte) in a sample, particularly an analyte present trace amounts in a biological sample. Most of such trace analytes are generally contained in the sample only in an amount of a μg/ml unit or less. For example, there is a detectability limitation in an immunodiffusion or laser nephelometer method, wherein a complex produced from an antigen-antibody reaction is directly measured. Therefore, such trace analytes in the biological sample may be measured more accurately by a method, wherein one of the antigen or antibody is labeled with a suitable substance and a signal originating therefrom is detected, namely, a label-immunoassay, or the like. The label-immunoassay may be carried out in many ways. For example, there may be mentioned a forward sandwich assay or a delayed one-step sandwich assay. The one-step sandwich assay can be carried out using the following steps: (1) a sample is brought into contact with an insoluble carrier covered with a first immunological partner of an analyte; (2) after a washing treatment is optionally carried out, the resulting first immunological partner-analyte-complex carried on the insoluble carrier is brought into contact with a labeled second immunological partner; (3) the resulting complex of the insoluble carrier-first immunological partner-analyte-labeled second immunological partner, and a portion not containing said complex are separated; and (4) a signal originating from the label contained in one of the complex or the portion without said complex is detected. A one-step sandwich assay may also be carried out using the following steps: (1) a sample is brought into contact with an insoluble carrier covered with a first immunological partner of an analyte, and at the same time with a labeled second immunological partner; (2) the resulting complex of the insoluble carrier-first immunological partner-analyte-labeled second immunological partner, and a portion not containing said complex are separated; and (3) a signal originating from the label contained in one of the complex or the portion without said complex is detected. A reverse sandwich assay may also be carried out using the following steps: (1) a sample is brought into contact with a labeled first immunological partner of an analyte; (2) the resulting labeled first immunological partner-analyte-complex is brought into contact with a second immunological partner carried on an insoluble carrier; (3) the resulting complex of the labeled first immunological partner-analyte-second immunological partner-insoluble carrier, and a portion not containing said complex are separated; and (4) a signal originating from the label contained in one of the complex or the portion without said complex is detected. An immunoinhibition method may also be carried out using the following steps: (1) a sample is brought into contact with a labeled first immunological partner (preferably a labeled monoclonal antibody in case of an antibody) of an analyte, and then with a substance which shows a function same as that of the analyte and is carried on an insoluble carrier, or an immunological partner to the analyte, said partner being carried on an insoluble carrier; (2) the resulting immunological partner-substance showing the function same as that of the analyte-insoluble carrier complex, and a portion not containing said complex are separated; (3) and a signal originating from the label contained in one of the complex or the portion without said complex is detected. A competitive method may also be carried out using the following steps: (1) a sample is competitively brought into contact with an insoluble carrier covered with an immunological partner to an analyte, and a substance which shows a function the same as that of the analyte; (2) the resulting insoluble carrier-immunological partner-substance showing the function the same as that of the analyte complex, and a portion not containing said complex are separated; (3) and a signal originating from the label contained in one of the complex or the portion without said complex is detected.

Further, the label-immunoassay may be classified, in view of the label used, under, for example, an EIA wherein an enzyme is used as a label, an immunoagglutination method wherein erythrocytes or latex particles are used as a carrier, and the resulting aggregates are visually observed, RIA wherein an isotope is used as a label and the like. In these methods, the amount of the complex produced is increased with the contacting time of the sample with the immunological partner to the analyte. Therefore, the contacting of the sample with the immunological partner is lengthily continued to reach the equilibrium state, namely until the amount of the complex produced is not changed.

The RIA method requires particular equipment and has a problem of radioactive wastes, and thus, has gradually been replaced with the EIA method or the like. Further, when a blood sample is used in all the above-mentioned conventional methods, the collected whole blood sample was not used as they are, but a serum or plasma sample was prepared from the collected whole blood, and then an assay was carried out. When a whole blood sample containing insoluble components such as hemocytes is used in general methods other than the above methods, the insoluble components would possibly interfere with the value measured. For example, when the lights as detecting signals originating from the labels are measured in a visible light range in a homogeneous assay wherein B/F separation is not carried out, a value with a positive error may be obtained. In agglutination, an accurate determination cannot be carried out, because substances, such as hemocytes, which produce turbidity independently of the desired agglutination exist. On the other hand, the B/F separation assay may be conducted by reacting a whole blood sample with an antibody immobilized on an insoluble carrier, washing out the whole blood, and then reacting with a labeled antibody or the like. However, the result of the above assay is different from that of an assay using a serum sample, because there exist a lot of hemocyte components in the whole blood. Further, the results cannot be adjusted by multiplying a constant coefficient, because each individual has a different amount of hemocytes. Therefore, the result obtained from a whole blood sample should be adjusted by measuring a hematocrit value of the blood examined so as to obtain a diagnostic criterion from the whole blood sample. Taking into account such troublesome procedure, a serum or plasma sample prepared from a whole blood sample was used even in an assay wherein B/F separation was carried out.

Many attempts to avoid the influence of the insoluble components have been made. For example, Japanese Examined Patent Publication (Kokoku) No. 02-51150 discloses a method to avoid the influence of the insoluble components by adding a hemolyzing agent to whole blood before agglutination. Japanese Unexamined Patent Publication (Kokai) No. 01-237454 discloses a method to enhance detectability by enzymatic digestion or exposure to a mild acid to remove interfering substances and expose binding sites in a whole blood sample. Japanese Unexamined Patent Publication (Kokai) No. 01-165964 discloses a method to reduce the influence of the insoluble components by treating a whole blood with neuraminidase to liberate latent tumor-associated antigens. Further, as an attempt to conduct measurement without removing insoluble components, a method for detecting hepatitis virus by a dried filter blood is disclosed in Japanese Unexamined Patent Publication (Kokai) No. 64-63868. In this method, a filter paper stained with blood is air-dried, the dried filter paper is cut up to a piece with a predetermined surface area, and the piece, a buffer to extract the blood components contained the piece, and beads coated with antibodies are reacted for about 20 hours. However, the above method requires the pretreatment procedures of the air-drying of the blood on the filter paper and cutting of the dried paper. The above method does not use a whole blood sample as it is, but uses the blood components extracted from the filter paper.

In addition to the above-mentioned methods using immunoreaction in liquid, an analyte may be detected using a whole blood sample, by a method using a dry immunoassay element called dry chemistry [Japanese Unexamined Patent Publication (Kokai) No. 01-112159], a method using so-called biosensor [Japanese Unexamined Patent Publication (Kokai) No. 04-502671], or a method using immunochromatography [Japanese Unexamined Patent Publication (Kokai) No. 06-94718].

In the above-mentioned conventional methods wherein immunoreaction is carried out in liquid, an additional procedure (pretreatment) is required before the immunoreaction, and thus the assay procedure becomes troublesome. In many cases, the above methods are not suitable for treating many samples for many examination items. The method using a dry immunoassay element and a whole blood sample is not satisfied with accuracy. The methods using a biosensor or immunochromatography require particular equipment.

Accordingly, the object of the present invention is to provide an assaying means capable of rapidly measuring an analyte in a whole blood sample, using a whole blood as a sample without pretreatment of the blood. More particularly, the object is to provide an assaying means capable of obtaining a result for an analyte from a whole blood sample, identical to that from a conventional sample, such as serum or plasma, even when a problem associated with the whole blood sample, such as troublesome variation of existing ratio of insoluble components and soluble components, is encountered, to thereby enable a rapid examination without pretreatment of the collected whole blood sample, and extremely save labor in a general examination.

DISCLOSURE OF INVENTION

According to the present invention, a concentration of a substance to be examined (analyte) in a whole blood sample can be determined using a simple and rapid assay, particularly an immunoassay, as in a method wherein a serum or plasma sample is used. Thus, the procedure of separating serum or plasma becomes unnecessary. Further a whole blood sample is brought into contact with an insoluble carrier coated with specifically binding partners (particularly immunological partners) for a short period of time in the present invention, and thus, a result can be obtained rapidly.

The above object can be achieved by the present invention relating to a method for measuring a substance to be examined (analyte), characterized in that a sufficient amount of a whole blood sample is brought into contact with an insoluble carrier coated with a first partner specifically bindable to said substance to be examined (analyte) for a short period of time; a complex of said substance to be examined (analyte) and said first partner is brought into contact with a second partner which is labeled and capable of specifically binding to said first partner, said complex being carried on said insoluble carrier; a resulting complex of said insoluble carrier-said first partner-said substance to be examined (analyte)-said labeled second partner, and a portion without said resulting complex are separated from eath other; and a signal originating from said label contained in one of said separated portions is detected. The first partner may be same as or different from the second partner. The first and second partners may appropriately be selected on the basis of the analyte.

BEST MODE FOR CARRYING OUT THE INVENTION

The present invention will be described in detail hereinafter.

The present invention comprises using a whole blood sample taken from a patient or the like by any processes, such as blood collection, or a synthetic sample containing an analyte or an analogue thereof, and immunologically measuring the analyte in said sample. The term "whole blood sample" used herein means a sample which has not been treated to remove insoluble components from blood taken from a patient or the like, and thus contains insoluble components. Therefore, a serum sample or a plasma sample is not involved in the whole blood sample. The whole blood sample involves a sample prepared by adding, to a collected blood, an anticoagulant, such as EDTA, sodium citrate, heparin, sodium fluoride, or sodium oxalate, and/or a blood preservative, such as CPD comprising sodium citrate, citric acid, glucose and sodium dihydrogenphosphate, or the like. Further, a sample prepared by diluting a blood collected from a patient or the like with, for example, a buffer having an anticoagulant function is also involved in the above whole blood sample. A sample prepared by treating a blood collected from a patient or the like as in the above manner, and allowing to stand for a long period of time, for example, for a durable term of a blood preservative, i.e., for 21 days or more at 4 to 6° C., is also involved in the above whole blood sample. The "synthetic sample containing an analyte or an analogue thereof " is a sample for use of quantitative determination of the present invention, or for control of accuracy of the present invention. The synthetic sample may contain or need not contain natural or synthetic insoluble components, such as hemocytes, latex beads or the like. Preferably, the synthetic sample does not contain insoluble components in view of workability. Further, the synthetic sample need not contain an analyte or an analogue thereof, if it contains a substance which shows correlation with the analyte.

The analyte in the present invention is not limited, so long as it is generally contained in blood, particularly in a trace amount. There may be mentioned, for example, proteins, polysaccharides, lipids, haptens, nucleic acids, or a complex or fragment thereof. More particularly, the analyte is, for example, an infectious disease-related marker, such as an HBs antigen, HBs antibody, HIV-1 antibody, HIV-2 antibody, HTLV-I antibody or treponema antibody, a tumor-associated antigen, such as AFP, CRP or CEA, a coagulation-fibrinogenolysis-related marker, such as plasminogen, antithrombin-III, D-dimer or thrombin-antithrombin-III, a hormone, a cytosine, an enzyme, or a drug, such as antiepileptic or digoxin. Further, the analyte is also DNA or RNA having a specific sequence, or a polynucleotide fragment thereof.

The partner specifically binding to the analyte is a partner which immunologically binds specifically to the analyte, i.e., an immunological partner, for example, an immunological substance, such as an antigen or antibody, to proteins, polysaccharides, lipids, nucleic acids, or a complex or fragment thereof. For example, the partner is an antigen or antibody to the infectious disease-related marker, or an antibody to the tumor-associated antigen, more particularly an HBs antibody when the analyte is an HBs antigen an HIV-1 antigen when the analyte is an HIV-1 antibody. Further, when the analyte is a nucleic acid, the partner may be not only the antibody thereto, but also the complementary nucleic acid, such as complementary DNA or RNA, or a fragment thereof prepared by treating with a restriction enzyme, or a synthetic polynucleotide thereof, having at least a part of, preferably all of, the sequence complementary to that of the nucleic acid to be examined. The antibody as the immunological partner may be a monoclonal antibody or polyclonal antibody, or a fragment prepared by treating with an enzyme. An immunoglobulin which is not treated or treated with an enzyme, such as IgG or F(ab')$_2$ prepared by pepsin digestion, may be also used. As the antigen, a product obtained from a virus lysate by a common process, such as density gradient centrifugation, or a peptide or recombinant protein corresponding to a part of the antigen may be also used. The specifically binding partner without a label is immobilized to an insoluble carrier and used as the first specifically binding partner, and the specifically binding partner with a label is used as the second specifically binding partner. The present invention wherein immunological partners are used as the specifically binding partners will be described hereinafter. It is to be understood that the following description may also be applied to the present invention wherein the complementary nucleic acids are used as the specifically binding partners.

When the present invention is carried out, an insoluble carrier is coated with the first immunological partner to the analyte, for example, by a conventionally known process, such as the physical adsorption or covalent bond as described in "Koso-Meneki-Sokutei-Ho (Enzyme Immunoassay)". More particularly, the process comprises bringing the insoluble carrier into contact with a solution containing the immunological partner at room temperature for several hours, washing with an appropriate buffer, and if necessary, air-drying. After the carrier is coated with the immunological partner, if necessary, the carrier may be blocked with, for example, bovine serum albumin or skimmed milk, or excess functional groups may be blocked with, for example, lysine, to prevent components other than the analyte from adsorbing to the insoluble carrier. The resulting insoluble carrier coated with the immunological partner may be stored as it is, or as a swelled form in a suitable buffer, such as a phosphate buffer.

In the present invention, any known insoluble carrier, such as a tube, plate, membrane, film or bead, may be used. The carrier may be made of natural or synthetic material, such as cellulose, polyamide, polystyrene or polyethylene, or a combination thereof, or a material prepared by adding an inorganic material such as iron thereto to obtain a suitable strength. The surface of the insoluble carrier is preferably treated by a known process, for example, suitable anion groups are introduced to the surface, to prevent substances other than the analyte or the labeled immunological partner from nonspecifically adsorbing to the surface. Further, suitable functional groups, such as a carboxyl or amino group, are preferably introduced to the surface of the insoluble carrier by a known process so that the insoluble carrier may easily be coated with the immunological partner to the analyte. The bead as the immunological partner may be porous or nonporous, but nonporous one with good washability being preferable. The diameter of the bead is preferably 0.1 $\mu$m to 7 mm. When the bead is washed by filtration using a filter or suction using a nozzle, the bead having a diameter greater than those of insoluble components in a whole blood sample, for example, 10 $\mu$m or more, is more preferably used. The bead containing a magnetic material, such as ferrite, may be washed by collecting the beads by a magnet, without a filter, and thus the diameter of such bead may be 10 $\mu$m or less, preferably 0.1 to 5 $\mu$m.

The resulting immunological partner-coated insoluble carrier is then brought into contact with a whole blood sample to form a complex of the analyte and the immunological partner on the insoluble carrier. In this step of the present invention, it is preferable that a lot of liquid substances, such as a buffer for diluting the sample, are not contained.

An assay system wherein an immunoreaction is carried out for a long period of time is generally called an end-point assay, and is based on the completion of the immunoreaction of all the analyte in the sample added to the assay system. When a whole blood having a hematocrit value of 30% is used as a sample in this assay, the amount of the analyte is 70% of that contained in the same amount of the serum, and thus the result would be found to be 70% of that obtained from the corresponding assay using the same amount of the serum sample. If a whole blood having a hematocrit value of 50% is used as a sample in this assay, the result would be found to be 50% of that obtained from the corresponding assay using the same amount of the serum sample. Therefore, an adjustment by a hematocrit value must be made so as to secure interchangeability of the result with that obtained from the assay using a serum sample.

On the contrary, the present invention is characterized in that a whole blood sample is brought into contact with the immunological partner-coated insoluble carrier for a short period of time from an initial stage of the reaction, and the reaction is ceased or the measuring is carried out before the end-point of the reaction. Thus, all the analytes in the sample are not reacted with the immunological partners on the insoluble carriers, but the analytes are reacted with the partners within a limited time in an amount dependent on and proportional to the concentration of the analytes. In this case, the concentration of the analyte in a whole blood is same as that in a serum. Therefore, the hemocytes present in the sample do not interfere with the results. The result obtained from a whole blood sample is unexpectedly excellently corresponding to that obtained from a serum sample.

The concrete contacting time varies with a kind or concentration of the analyte used, a kind of the immunological partners used, a surface area of the insoluble carrier, or the like. The reaction time range within which the result from a whole blood sample is identical to that from a serum or plasma sample obtained from said whole blood may be easily determined by a simple pilot test.

The whole blood sample may be brought into contact with beads used as the insoluble carrier in such an amount that the beads are freely movable therein. The amount of the whole blood sample brought into contact with the insoluble carrier coated with the immunological partner may be determined by the following test.

For example, when the analyte is an antigen and the immunological partner thereof is an antibody, polystyrene beads (diameter=100 μm) are coated with a predetermined amount of the antibodies, and an assay is carried out with changing the amount of the whole blood sample and the reaction time for a predetermined constant amount of beads. Then, the conditions to obtain the results identical to those from a serum sample may be found.

For example, when an HBs antigen is used as the analyte, 1.7 μg and 0.12 μg of anti-HBs rabbit-specific antibodies F(ab')$_2$ are used as the first and second immunological partners, respectively, and 5 mg of polystyrene beads (diameter=100 μm; surface area=2.5 cm$^2$) are used as the insoluble carrier, the contacting time may be 24 hours or less, preferably 30 seconds to 30 minutes, more preferably 1 to 10 minutes.

A complex of the analyte in the whole blood sample and the first immunological partner on the insoluble carrier is formed by said contact, and then, washed with a phosphate buffer or the like, if necessary. It is not necessary, but preferable to perform the washing. This is because that if a buffer containing the labeled second immunological partner is used upon adding the second partner in the next step, the whole blood sample is diluted with the buffer, and the amount of the analyte is substantially changed. On the contrary to the former step, however, it is possible to minimize the influence of other liquid components in which the second immunological partner may be contained. For example, the influence may be reduced by adding the labeled second immunological partner after the analyte in the sample and the immunological partner on the insoluble carrier nearly reach a state of equilibrium, or adding the buffer containing the labeled second immunological partner in an amount smaller than that of the whole blood sample. The influence may be further reduced by combining the above two methods. It is not necessary to perform the washing procedure, when the labeled second immunological partner is a powder material, or powdery partners are encapsulated. If the washing is performed, the buffer containing the labeled second immunological partner used upon adding the second partner in the next step does not affect that the result of the whole blood sample is made identical to the result of the serum or plasma sample obtained from said whole blood sample.

In the next step, the second immunological partner labeled with a suitable labeling material is brought into contact with the complex. The contacting time of the labeled second immunological partner with the complex of the immunological partner-coated insoluble carrier and the analyte is not particularly limited, but may be several hours or less as in a conventional method. In view of a rapid assay, the contacting time is 1 hour or less, preferably 30 minutes or less, more preferably 10 minutes or less. In this step, a complex of the immunological partner on the insoluble carrier/the analyte/the labeled second immunological partner is formed, and washed with a suitable buffer to remove unbound portion of the labeled second immunological partner.

In the present invention, any conventionally known labeling materials may be used. For example, an enzyme, such as peroxidase or alkaline phosphatase, a bioluminescent substance, such as luciferin-luciferase, a chemiluminescent substance, such as luminol, acridine derivative or adamantane derivative, fluorescent substance, such as fluorescein isothiocyanate, a metal, such as gold colloid, a radioactive material, such as $^{32}$P, or the like may be used as a label. The label may be sensitized with an enzyme cycling or the like. It is preferable to use the chemiluminescent substance, such as luminol, acridine derivative or adamantane derivative.

The second immunological partner may be labeled with the labeling material by a known process. For example, the labeling material may be bound to the second immunological partner by a physical-binding method wherein the material and the partner are directly admixed, a glutaraldehyde method wherein the material and the partner are bound via a suitable linker, a periodate method, a maleimide method, a pyridine-disulfide method, a method wherein the material and the partner are bound via an avidin and biotin, or the like. The resulting labeled material may be stored in a suitable solution, or preferably phosphate buffer. The necessary amount of the solution may be added to the complex, after diluted if necessary. In this stage, a conventionally known blocking agent, such as bovine serum albumin or skimmed milk, a preservative, such as sodium azide, or a signal-amplifying agent, such as p-iode-phenol may be added.

The complex of the immunological partner on the insoluble carrier/the analyte/the labeled second immunological partner which is formed in the former step is washed with a suitable buffer, to separate a portion containing the complex (washed residue) and the other portion not containing the complex (washings). Then, the signal originating from the label in one of the separated portions, preferably the portion containing the complex (washed residue) may be detected to qualitatively or quantitatively determine the analyte in the sample.

When an enzyme is used as the label, a substrate and chromogene or the like may be added. After the reaction is performed in a predetermined term, a color strength may be spectroscopically measured. When a chemiluminescent substance, such as an acridine derivative, is used as the label, hydrogen peroxide and an alkaline solution by which the acridine derivative emits may be added, at the same time or separately. After the reaction is performed in a predetermined term, an intensity of chemiluminescence may be measured by a photomultiplier. In this case, a signal-amplifying agent, such as hydrochloric acid, may be added if necessary, before the addition of hydrogen peroxide and the alkaline solution, or together with hydrogen peroxide. The analyte in the whole blood sample may be measured in a short period of time by measuring the resulting signal originating from the label.

According to the present invention, as explained above, the analyte in the whole blood sample may be quickly measured, using the whole blood without pretreatment, as a sample. Further, the present invention can shorten the contacting time of the sample and the immunological partner. Furthermore, a surprisingly advantageous effect that the analyte result from the whole blood sample shows a correlation with the analyte result from the conventional sample, such as a serum or plasma sample, can be obtained by selecting preferable conditions of the contacting time, the amount of the sample, the amount of the insoluble carrier (the surface area of the carrier or the amount of the immunological partner coated), and so on. Because the pretreatment of the collected blood which is required in conventional methods may be omitted, and the contacting time may be shortened as above, thus, the present invention can achieve a rapid examination and an extreme labor-saving in a general examination. The present invention may be applied not only to the above forward sandwich assay or delayed one-step sandwich assay, but also to all the general label-immunoassays, such as a one-step sandwich assay, reverse sandwich assay, or competitive assay. The sample which may be used in the present invention is not limited only to the whole blood sample, but the other biological components, such as serum, plasma, urine, or the like may be measured.

EXAMPLE

The present invention now will be further illustrated by, but is by no means limited to, the following examples.

Example 1

Preparation of Beads Coated with Anti-HBs Antibodies

The antiserum obtained from a rabbit immunized with HBs antigens was purified as follows. The antiserum was treated with an HBs antigen-immobilized Sepharose 4B column, and the unbound serum components were thoroughly washed with 20 mM phosphate buffer, pH 7.0 (hereinafter referred to as PBS) containing 0.15 M NaCl. Then, the specific antibodies were eluted by PBS containing 3M sodium thiocyanate, and the elute was dialyzed to 50 mM acetate buffer (pH 4.5). The specific antibodies were digested with 2% by weight (based on the antibodies weight) of pepsin at 37° C. for 16 hours. 1 M tris solution was added and pH was adjusted to pH 8 to cease the reaction. Thereafter, F(ab')$_2$ was fractionated through Sephacryl S-200 column (equilibrated with PBS). The resulting anti-HBs specific antibody F(ab')$_2$ fraction was diluted with PBS to 100 µg/ml. Polystyrene beads (diameter =100 µm) were added thereto in an amount of 0.35 g/1 ml of the antibody solution, and admixed therewith by a rotator at 37° C. for 4 hours to obtain coated beads. The beads was washed with PBS three times, and stored in the form of 10% suspension in PBS.

Example 2

Preparation of Acridinium Ester-labeled Anti-HBs Antibodies

The anti-HBs antibody F (ab')$_2$ fraction prepared in Example 1 was diluted with 0.1 M phosphate buffer (pH 8.0) to 0.25 mg/ml. To the antibody liquid (1 ml), a solution (50 µl) of 0.125 mg/ml 10-methyl-9-{4-[2-(succinimidyloxycarbonyl)-ethyl]phenyloxycarbonyl}-acridinium fluorosulfonate in dimethylformamide was added. The reaction was performed under shaking at room temperature for 30 minutes. Thereafter, 0.5 ml of 0.2 M glycine buffer (pH 8.0) as a blocking agent was added, and the reaction was performed under shaking for further 1 hour. The reaction mixture was treated through PD-10 column (Pharmacia) equilibrated with physiological salt solution to remove low-molecular luminescent substances.

Example 3

Measurement of HBs Antigen Concentrations in Whole Blood Sample

From the HBs antibodies-coated beads containing suspension prepared in Example 1, an aliquot containing 5 mg of the beads was taken by a pipette to a reaction vessel. 100 µl of a whole blood sample with EDTA was added thereto and the reaction was performed at 37° C. for 3 minutes under shaking. The reaction mixture was washed with a washing solution (10 mM phosphate buffer, pH 7.0, containing 0.15 M NaCl and 0.1% Tween 20) four times. After adding thereto 100 µl of a liquid prepared by diluting the luminescent substance-labeled HBs antibody prepared in Example 2 with the above washing solution to 1/100 and 200 µl of a dilution solution (PBS containing 0.05% Tween 20), the reaction was performed at 37° C. for 5 minutes under shaking. Then, the reaction mixture was washed with the washing solution four times. Emission was caused by adding 100 µl of 0.1 N-HCl aqueous solution and then 300 µl of 0.1 M sodium hydroxide solution containing 20 mM hydrogen peroxide. The chemiluminescent intensity was measured by a photomultiplier.

As a control test, the above procedure was repeated except that the serum sample prepared from the above whole blood sample was used, and the chemiluminescent intensity was obtained. The correlation between the serum sample and the whole blood sample was determined. The coefficient of correlation for 287 samples was 0.9958, and the regression line was y=0.9863 x+114 (x=serum; y=whole blood). The chemiluminescent intensities of both cases were well correlated.

Example 4

Changes in Result of HBs Antigen Concentration for Standing Time of Whole Blood Samples The whole blood samples were taken from the HBs-negative and HBs-positive patients by a blood collecting tube with adding EDTA (Terumo) and placed into test tubes in an amount of 5 ml. After allowing to stand for 15 minutes, 30 minutes, or 60 minutes, the procedure described in Example 3 was repeated, and a chemiluminescent intensity originating from the HBs antigen. The whole blood samples were stirred only shortly after collected, but allowed to stand at room temperature. The results are shown in Table 1.

TABLE 1

| | chemiluminescent intensities (counts) after blood collection (minutes) | | | |
|---|---|---|---|---|
| | 0 min later | 15 min later | 30 min later | 60 min later |
| HBs-negative sample | 2,185 | 2,159 | 2,226 | 2,148 |
| HBs-positive sample | 46,666 | 46,270 | 46,136 | 47,253 |

The precipitation of the hemocytes was visually observed while time elapsed after the whole samples were placed into the test tubes. However, substantial differences due to the standing time were not observed. When the immunoassay procedure was carried out, 100 µl of aliquot was taken from the sample in the test tube, at the position of 3 mm under the liquid level thereof.

Example 5

Preparation of HBs Antigen-coated Beads

HBs antigen-positive human plasma was fractionated by density gradient centrifugation (density of cesium chloride= 1.04 to 1.20; 48000 rpm; 210 minutes) to obtain virus particles. The virus particles were solubilized with Tween 80 to obtain the HBs antigen. Electrophoresis of the solubilized HBs antigen revealed that it mainly contained HBs antigen proteins having molecular weights of 24,000 and 27,000. The HBs antigen was diluted with 0.1 M glycine-NaOH buffer to 40 μg/ml. To 1 ml of the dilution, 0.35 g of styrene beads (diameter=100 μm) was added, and the whole was stirred at 37° C. for 16 hours to coat the beads with the antigens. The coated beads were washed with PBS five times, and stored as 10% suspension in PBS.

Example 6

Preparation of Acridinium Ester-labeled HBs Antigens

The HBs antigen prepared in Example 5 was diluted with 0.1 M phosphate buffer (pH 8.0) to 0.25 mg/ml. To the antigen liquid (1 ml), a solution (50 μl) of 0.125 mg/ml 10-methyl-9-{4-[2-(succinimidyloxycarbonyl)-ethyl]phenyloxycarbonyl}-acridinium fluorosulfonate in dimethylformamide was added. The reaction was performed under shaking at room temperature for 30 minutes. Thereafter, 0.5 ml of 0.2 M glycine buffer (pH 8.0) as a blocking agent was added, and the reaction was performed under shaking for further 1 hour. The reaction mixture was dialyzed to physiological salt solution three times to prepare the luminescent substance-labeled HBS antigen.

Example 7

Measurement of HBs Antibody Concentrations in Whole Blood Sample

From the HBS antigens-coated beads containing suspension prepared in Example 5, an aliquot containing 5 mg of the beads was taken by a pipette to a reaction vessel. 100 μl of a whole blood sample with EDTA was added thereto and the reaction was performed at 37° C. for 5 minutes under shaking. Then, 50 μl of a liquid prepared by diluting the luminescent substance-labeled HBs antigen prepared in Example 6 with the above washing solution to 1/100, and the reaction was performed for 5 minutes under shaking. The reaction mixture was washed with the washing solution four times. Emission was caused by adding 100 μl of 0.1 N-HCl aqueous solution and then 300 μl of 0.1 N sodium hydroxide solution containing 20 mM hydrogen peroxide. The chemiluminescent intensity was measured by a photomultiplier.

As a control test, the above procedure was repeated except that the serum sample prepared from the above whole blood sample was used, and the chemiluminescent intensity was obtained. The correlation between the serum sample and the whole blood sample was determined. The coefficient of correlation for 286 samples was 0.9927, and the regression line was y=1.017 x+207 (x=serum; y=whole blood). The chemiluminescent intensities of both cases were well correlated.

Example 8

Preparation of Anti-HBs Antibody-coated Magnetic Beads

Magnetic beads (tosylation-activated Dynabeads; particle size=0.5 μm; 2 ml) were collected by a magnet (MPC) to remove the supernatant. The beads were washed by adding 4 ml of 50 mM borate buffer (pH 9.5), and then collected by MPC. The supernatant was removed with suction, and 1 ml of the above buffer was added to the beads to obtain the suspension.

The anti-HBs-specific antibody F(ab')$_2$ fraction prepared in Example 1 was dialyzed to 50 mM borate buffer (pH 9.5). To 1 ml of the antibody liquid prepared by adjusting the concentration to 0.5 mg/ml, the bead suspension was added dropwise, and admixed with gently stirring in an incubator at 37° C. for 24 hours. After the beads were collected by the MPC, the supernatant was removed with suction. To the beads, 4 ml of bovine serum albumin (BSA) liquid prepared by adjusting the concentration to 1 mg/ml with 20 mM phosphate buffer (pH 7.0) containing 0.15 M NaCl was added, and the whole was stirred at 4° C. overnight to block the excess functional groups. After washed with PBS four times as above, the beads were stored in 2 ml of PBS containing 0.05% sodium azide and 1 mg/ml BSA.

Example 9

Relation Between Reaction Time and HBs Antigen Concentrations

From the HBs antibodies-coated beads containing suspension prepared in Example 1, an aliquot containing 5 mg of the beads was taken by a pipette to a reaction vessel. 100 μl of a whole blood sample with EDTA (HBs antigen=25 U/ml) was added thereto and the reaction was performed at 37° C. for 1 minute, 3 minutes, 5 minutes, 15 minutes, 30 minutes, 1 hour, 3 hours, 7 hours, 24 hours, or 48 hours under shaking. The reaction mixture was washed with a washing solution (10 mM phosphate buffer, pH 7.0, containing 0.15 M NaCl and 0.1% Tween 20) four times. After adding thereto 100 μl of a liquid prepared by diluting the luminescent substance-labeled HBs antibody prepared in Example 2 with the above washing solution to 1/100 and 200 μl of a dilution solution (PBS containing 0.05% Tween 20), the reaction was performed at 37° C. for 5 minutes under shaking. Then, the reaction mixture was washed with the washing solution four times. Emission was caused by adding 100 μl of 0.1 N HCl aqueous solution and then 300 μl of 0.1 M sodium hydroxide solution containing 20 mM hydrogen peroxide. The chemiluminescent intensity was measured by a photomultiplier.

As a control test, the above procedure was repeated except that the serum sample prepared from the above whole blood. The results are shown in Table 2. It is apparent from Table 2 that the measurements (chemiluminescent intensities) are almost the same within 1 to 30 minutes of the contacting time of the sample and the antibody-beads, between the EDTA-added whole blood sample and the serum sample separated therefrom.

TABLE 2

| Time | Whole blood | Serum |
| --- | --- | --- |
| 1 minute | 6114 | 5850 |
| 3 minutes | 16026 | 16164 |
| 5 minutes | 25060 | 24940 |
| 15 minutes | 52368 | 53176 |
| 30 minutes | 79953 | 87234 |
| 1 hour | 92035 | 121869 |
| 3 hours | 108694 | 145286 |
| 7 hours | 113945 | 169346 |
| 24 hours | 116523 | 172345 |
| 48 hours | 118692 | 176692 |

Example 10

Relation Between HBs Antigen Concentrations and Hematocrit Values

A blood sample was taken from an HBs-positive patient by a blood collecting tube with adding EDTA (Terumo) and the hematocrit value thereof was adjusted to 70%. Then, the blood samples having hematocrit values of 0%, 10%, 20%, 30%, 40%, 50%, 60%, and 70% were prepared by diluting the whole blood sample with the plasma taken from the same patient. Then, the procedure described in Example 3 was repeated, and a chemiluminescent intensity originating from the HBs antigen was measured. The results are shown in Table 3. In this Example, blood samples having hematocrit values of more than 70% were not used, because such samples were difficult to be collected.

Example 11

Changes of HBs Antigen Concentrations by Diluting Samples

From the HBs antibodies-coated beads containing suspension prepared in Example 1, an aliquot containing 5 mg of the beads was taken by a pipette to a reaction vessel. Further, 100 μl of each of the whole blood samples prepared by diluting to have the above hematocrit values as in Example 10, and 100 μl of the washing solution used in Example 3 were added thereto. Then, the procedure described in Example 3 was repeated, and a chemiluminescent intensity originating from the HBs antigen was measured. The results are shown in Table 3.

Example 12

Changes of HBs Antigen Concentrations Without Primary Washing (1)

From the HBs antibodies-coated beads containing suspension prepared in Example 1, an aliquot containing 5 mg of the beads was taken by a pipette to a reaction vessel. Further, 100 μl of each of the whole blood samples prepared by diluting to have the above hematocrit values as in Example 10 was added thereto, and the reaction was performed at 37° C. for 5 minutes under shaking. After adding to the reaction mixture 100 μl of a liquid prepared by diluting the luminescent substance-labeled HBs antibody prepared in Example 2 with the washing solution used in Example 3 to 1/100 and 100 μl of a dilution solution (PBS containing 0.05% Tween 20), the reaction was performed at 37° C. for 5 minutes under shaking. Then, the procedure described in Example 3 was repeated, and a chemiluminescent intensity originating from the HBs antigen was measured. The results are shown in Table 3.

Example 13

Changes of HBs Antigen Concentrations Without Primary Washing (2)

From the HBs antibodies-coated beads containing suspension prepared in Example 1, an aliquot containing 5 mg of the beads was taken by a pipette to a reaction vessel. Further, 100 μl of each of the whole blood samples prepared by diluting to have the above hematocrit values as in Example 12 was added thereto, and the reaction was performed at 37° C. for 5 minutes under shaking. After adding to the reaction mixture 10 μl of a liquid prepared by diluting the luminescent substance-labeled HBs antibody prepared in Example 2 with the washing solution used in Example 3 to 1/27.5, the reaction was performed at 37° C. for 5 minutes under shaking. Then, the procedure described in Example 3 was repeated, and a chemiluminescent intensity originating from the HBs antigen was measured. The results are shown in Table 3.

TABLE 3

| Hematocrit value | Example 10 | Example 11 | Example 12 | Example 13 |
| --- | --- | --- | --- | --- |
| 0% | 17764 | 17566 | 16486 | 18182 |
| 10% | 17506 | 16376 | 16284 | 18286 |
| 20% | 17682 | 15250 | 15752 | 17978 |
| 80% | 17340 | 14122 | 15426 | 18000 |
| 40% | 17982 | 12874 | 14876 | 17620 |
| 50% | 17860 | 11700 | 14720 | 17782 |
| 60% | 17886 | 10258 | 14450 | 17894 |
| 70% | 17368 | 7974 | 13118 | 17460 |

(Figures are emission counts)

From the results of Examples 10 to 13, it was confirmed that hematocrit value does not produce a difference of or does not affect the emission, if other liquid components are absent upon contacting the whole blood sample containing the HBs antigens and the beads coated with HBs antibodies (Example 10); and that the changes in the measurements due to the hematocrit values are very small when the HBs antibodies labeled with acridinium esters were added in a 1/10 th amount of the sample, after contacting the whole blood sample containing the HBs antigens and the beads coated with HBs antibodies, but not carrying out the washing procedure (Example 13). The reason is assumed that the formation of the complex of the HBS antigen in the whole blood sample and the HBs antibodies-coated bead proceeds before the HBs antibodies labeled with acridinium esters were added, and the influence by the addition is very small in comparison with that to the measurements by the change of the sample calculated from hematocrit value.

Example 14

Measurement of HBS Antigen Concentrations in Whole Blood Sample Using Magnetic Beads The suspension (50 μl) of the HBs antibodies-coated magnetic beads prepared in Example 8 was placed in a reaction vessel, and collected by the MPC to remove liquid components with suction. After adding 100 μl of the whole blood sample with added EDTA, the whole was reacted at 37° C. for 3 minutes under shaking. The reaction mixture was washed with the washing solution described in Example 3 four times. After adding thereto 100 μl of a liquid prepared by diluting the luminescent substance-labeled HBS antibody prepared in Example 2 with the above washing solution to 1/100 and 200 μl of the dilution solution described in Example 3, the reaction was performed at 37° C. for 5 minutes under shaking. Then, the reaction mixture was washed with the washing solution four times. Emission was caused by adding 100 μl of 0.1 N HCl aqueous solution and then 300 μl of 0.1 M sodium hydroxide solution containing 20 mM hydrogen peroxide. The chemiluminescent intensity was measured by a photomultiplier. As a control test, the above procedure was repeated except that the serum sample prepared from the above whole blood, and the chemiluminescent intensity was measured. The coefficient of correlation for 50 samples was 0.9892, and the regression line was y = 0.9739 x +189 (x = serum; y = whole blood). The chemiluminescent intensities of both cases were well correlated.

INDUSTRIAL APPLICABILITY

According to the present invention, the whole blood can be used as a sample without pretreatment, and the analyte in the whole blood sample can be quickly measured. Therefore, the present invention enables a rapid examination without the pretreatment of the collected blood which is required in conventional methods, and achieves an extreme labor-saving in a general examination.

As above, the present invention was explained with reference to particular embodiments, but modifications and improvements obvious to those skilled in the art are included in the scope of the present invention.

What is claimed is:

1. A method for quantitatively measuring an analyte in an undiluted whole blood sample comprising the steps of:

(A) contacting an undiluted whole blood sample comprising said analyte with magnetically-responsive particles, wherein said particles comprise a first partner which is coated on a magnetically-responsive particulate insoluble carrier, wherein said first partner specifically binds to said analyte to form a first complex of insoluble carrier-first partner-analyte;

(B) separating the resulting first complex of step (A) from the undiluted whole blood sample;

(C) contacting the resulting separated first complex of step (B) with a second partner, wherein said second partner is labeled with a detectable marker and specifically binds to said analyte to form a second complex of insoluble carrier-first partner-analyte-second partner;

(D) separating the resulting second complex of step (C) from unbound second partner by washing; and (E) detecting said marker in said second complex to quantitatively measure said analyte in said undiluted whole blood sample, wherein said contacting in step (A) occurs by dispersing said particulate insoluble carrier in said undiluted whole blood sample without substantially diluting said undiluted whole blood sample, and wherein said contacting in step (A) occurs for a period of time prior to an end-point of the binding reaction of said first partner and said analyte.

2. The method of claim 1, wherein said contacting in step (A) is carried out for not more than 30 minutes.

3. The method of claim 1, wherein said first partner and said second partner are immunological substances.

4. The method of claim 3, wherein said marker is a chemiluminescent substance.

5. The method of claim 3, wherein said marker is an enzyme.

6. The method of claim 1, 2, 3, 4 or 5, wherein said analyte is Hepatitis B surface antigen.

* * * * *